US007867700B2

(12) United States Patent
Fang et al.

(10) Patent No.: US 7,867,700 B2
(45) Date of Patent: Jan. 11, 2011

(54) POROUS SUBSTRATE PLATES AND THE USE THEREOF

(75) Inventors: Ye Fang, Pained Post, NY (US); Ann M. Ferrie, Painted Post, NY (US); Yulong Hong, Painted Post, NY (US); Brian L. Webb, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 383 days.

(21) Appl. No.: 11/870,742

(22) Filed: Oct. 11, 2007

(65) Prior Publication Data

US 2008/0119370 A1 May 22, 2008

Related U.S. Application Data

(62) Division of application No. 10/822,385, filed on Apr. 12, 2004, now Pat. No. 7,384,779.

(51) Int. Cl.
*C12Q 1/00* (2006.01)

(52) U.S. Cl. ............................ 435/4; 422/58; 436/809

(58) Field of Classification Search ...................... None
See application file for complete search history.

(56) References Cited

U.S. PATENT DOCUMENTS 4,544,395 A 10/1985 Evans ........................ 65/60.3
4,770,856 A 9/1988 Uthemann et al. .......... 422/104
4,948,564 A 8/1990 Root et al. .................. 422/101
5,084,246 A * 1/1992 Lyman et al. .............. 422/101
5,585,136 A 12/1996 Barrow et al. ............. 427/2.24
5,679,310 A 10/1997 Manns ....................... 422/102
5,770,722 A 6/1998 Lockhart et al. .......... 536/25.3
5,807,522 A 9/1998 Brown et al. .................. 422/50
5,843,789 A 12/1998 Nomura et al. ............ 436/164
5,861,306 A 1/1999 Pugh et al. ............... 435/288.4
5,959,098 A 9/1999 Goldberg et al. .......... 536/25.3
6,004,752 A 12/1999 Loewy et al. .................. 435/6
6,096,562 A 8/2000 Bunn et al. ................ 436/518
6,103,080 A 8/2000 Pham et al. ................ 204/424

(Continued)

FOREIGN PATENT DOCUMENTS

DE 100 59 328 11/2000

(Continued)

OTHER PUBLICATIONS

M. Glazer et al., “High Surface Area Substrates for DNA Arrays”, Mat. Res. Soc. Symp. Proc. vol. 576, 1999 Materials Research Society, pp. 371-375.

(Continued)

*Primary Examiner*—Christopher L Chin
(74) *Attorney, Agent, or Firm*—John L. Haack

(57) ABSTRACT

A substrate plate or device adapted for use with biological or chemical assays is disclosed. The device may take the form of a multi-well plate having a three-dimensional, porous layer as part of a support surface within each well for immobilizing probe species. The porous layer is characterized as having a plurality of interconnected voids defined by a matrix of contiguous solid material. A method and its variants are also described.

4 Claims, 8 Drawing Sheets
(4 of 8 Drawing Sheet(s) Filed in Color)

U.S. PATENT DOCUMENTS

| | | | | |
|---|---|---|---|---|
| 6,238,624 | B1 | 5/2001 | Heller et al. | 422/68.1 |
| 6,306,348 | B1 | 10/2001 | Havens et al. | 422/68.1 |
| 6,750,023 | B2 | 6/2004 | Tanner et al. | 435/6 |
| 6,824,866 | B1 | 11/2004 | Glazer et al. | 428/317.9 |
| 2002/0102578 | A1 | 8/2002 | Dickinson et al. | 435/6 |
| 2003/0232384 | A1* | 12/2003 | Kocher et al. | 435/7.1 |
| 2004/0022677 | A1 | 2/2004 | Wohlstadter et al. | 422/52 |

FOREIGN PATENT DOCUMENTS

| | | |
|---|---|---|
| GB | 2 400 332 | 10/2004 |
| WO | WO 00/61282 | 10/2000 |

OTHER PUBLICATIONS

Thomas H. Elmer, “Porous and Reconstructed Glasses”, Engineered Materials Handbook, vol. 4, The Materials Information Society, pp. 427-432.

M. Glazer et al., “Colloidal Silica Films for High-Capacity DNA Probe Arrays”, Chem. Mater, 2001, vol. 13, pp. 4773-4782.

* cited by examiner

A

B

A B

Figure 8
Mag = 50.00 K X
WD = 7 mm
EHT = 15.00 kV
Signal A = RBSD
100nm

POROUS SUBSTRATE PLATES AND THE USE THEREOF

This is a divisional of application Ser. No. 10/822,385, filed Apr. 12, 2004, entitled "POROUS SUBSTRATE PLATES AND THE USE THEREOF," now U.S. Pat. No. 7,384,779, issued Jun. 10, 2004.

FIELD OF THE INVENTION

The present invention relates to a substrate plate or device adapted for use with biological or chemical assays. More particularly, the present invention pertains to a multi-well plate having a three-dimensional or porous substrate as part of a support surface within each well.

BACKGROUND

In recent years, genomic-based assay techniques have uncovered many potential drug targets. This advance has lead to interest and development in the field of proteomics in general, and different kinds of screening assays in particular. Since genes encode for proteins, and proteins, in turn, perform nearly all of the life functions in a cell, then, virtually nothing is more important than deciphering the functions of proteins, because proteins are the targets against which most drugs are designed to act upon. Of the various approaches that have been proposed, array-based expression analysis and mutation mapping of many genes have made a major impact on biology and on drug discovery and development. Given that it is costly to sort out the multitude of chemical or drug targets one by one, this fact has created a demand for screening technologies that enable robust and parallel analysis of many targets.

Together with genomics, advanced chemical technologies and high-throughput screening, protein microarray technology has the potential to aid in understanding biological systems or system biology, as well as in developing new medicines of the future. Functional protein microarrays use native proteins as probes arranged on a substrate surface. Arrays of this type are useful for parallel studies of the activities of native proteins, such as protein-protein and protein-small molecule interactions. The interaction of proteins with a surface, however, complicates the preparation of protein microarrays. This problem arises because (i) proteins can denature at the interface between an aqueous solution and a solid surface, and (ii) random immobilization of proteins on a surface may cause the active site(s) of the proteins to be inaccessible for binding of targets. To achieve maximum binding capacity and desired stability of proteins on a surface with largely preserved structure and activity, the surface of solid supports generally need to be re-engineered. Examples include "deformable" polymer-grafted surfaces for immobilization of proteins (e.g., HydrogGel coated slides, PerkinElmer Life Science, Boston, Mass.), amine- or thiol-reactive surfaces for covalent coupling of proteins, or functional group-presenting surfaces for specific binding of proteins. Functional group-presenting surfaces include avidin-coated surfaces for biotinylated proteins, $Ni^{+2}$-chelating surfaces for histidine-tagged proteins, or antibody-modified surfaces for native proteins.

Traditionally, biological microarrays have been fabricated or printed on substrate surfaces that are largely two-dimensional, such as those of glass slides. Recently, porous substrates for biological microarrays have been proposed and reduced to practice. (See e.g., International Patent Applications No. WO0116376 A1, or WO0061282 A1, incorporated herein.) Porous substrates have several advantages over conventional two-dimensional substrates. These advantages include, for example, a higher loading capacity for probes in each microspot with an associated potential higher binding capacity, and generally, a higher binding specificity for target molecules, as well as greater accessibility of targets to the probes in each microspot, which increases the likelihood that a target reacts with its complement probe. This latter phenomenon, it is believed, is a result of the three-dimensional nature of a porous surface in which a significant portion of probes are captured in the micro- or nano-channels in the porous matrix.

Conventional porous slides or other substrates typically are constructed with a contiguous porous layer. In such a situation, even though individual microspots in an array may be distinct and physically separated from each other, the underlying porous matrix is not. This physically undifferentiated construction leads to problems associated with contamination or crosstalk. When multiple samples are applied to a single substrate, the sample solutions tend to spread and merge together by means of capillary wicking through underlying, interconnected channels in the porous substrate Hence, porous substrates have not readily been used for multiplexed assays on a single substrate. This limitation deprives the multiplexed applications of a readily available resource and its associated advantages.

The present invention overcomes the crosstalk problems, thereby extending the applications of porous substrates for bioassays using immobilized biological or chemical molecules for arrays in a microplate format. For instance, the production of identical DNA and protein arrays in the wells of a standard format microplate can be of great benefit for high-throughput analysis, as each resultant microplate will allow parallel processing of many different test samples against the same or different replicate biological arrays. In combining the unique properties of porous substrates with the high throughput capability of standard format microplates, one can achieve superior performance of surface-mediated bioassays including biological microarrays.

SUMMARY OF THE INVENTION

The present invention provides a device for performing multiple biological or chemical assays in parallel. The device addresses the problems of crosstalk and contamination associated with unitary porous bioassay substrates when multiple assay solutions or samples are applied onto the same substrate. As the invention overcomes the cross-talk issues, it can extend the applications of porous substrates into the calm of multiplexed biological assays in a microarray format. The device includes a substantially planar substrate that forms the bottom support of a microtiter well plate. The substrate has a number of individual porous patches or surfaces for attaching biological or chemical analytes. The individual porous patches form part of the bottom surface of each well. Since each porous patch is self-contained within a well, the likelihood of cross-contamination between wells by seepage or wicking is eliminated Each porous patch is adhered to a flat, rigid, non-porous understructure. The porous patch is characterized as having a plurality of open, interconnected voids of a predetermined mean size of not less than about 0.05 μm dispersed therethrough. The void channels extend through to a top surface of the porous patch. The voids are defined by a matrix or network of either contiguous or continuous material having a predetermined mean size of, preferably, not less than about 0.05 μm, and the solid material and contents of the voids exhibit a high contrast in their indices of refraction relative to each other. In other words, the porous patch may be characterized as having a rigid, three-dimensional, sponge-like structure, and can have a porosity of up to about 99.7%.

The porous surface can be derived from either a polymeric, organic material or an inorganic material having a granular morphology. When an inorganic material is used for the porous patch, the material is characterized as being non-absorbing and transparent to light, including infrared or ultraviolet radiation, when in the form of a solid of an amorphous or single crystal material, such as a glass or a metal oxide. More particularly for example, the material may be selected from a group consisting of a silicate, aluminosilicate, boroaluminosilicate, or borosilicate glass, or $TiO_3$, $SiO_2$, $Al_2O_3$, $Cr_2O_3$, CuO, ZnO, or $ZrO_2$.

In preferred embodiments, the porous surface is derived from a frit-based layer of individual particles, preferably having a coefficient of thermal expansion (CTE) compatible with that of an inorganic understructure (CTE±10-20%). Preferably the CTEs are matched. The substrate may further comprise a uniform coating of a binding agent over at least a part of the surface area of the voids and the top surface of the porous patch, and in some embodiments an interlayer disposed between the porous layer and the understructure. The interlayer has a coefficient-of-thermal-expansion compatible with the porous layer and the understructure, to prevent delamination of the porous layer from the understructure.

Each porous patch, preferably, has a thickness of at least about 5 μm. The matrix of inorganic material is formed by adhesion or sintering of the inorganic material particles to each other. The particles have a predetermined mean size preferably in the range of about 0.5 μm to about 5 μm, more preferably in the range of about 0.5 μm to about 3.5 μm. The voids within the porous inorganic layer have a predetermined mean size preferably in the range of about 0.5 μm to about 5 μm, and also, more preferably in the range of about 0.5 μm to about 3.5 μm. And, the content of the voids is either a gas, a liquid, or a solid.

According to an embodiment of the present inventive device, a porous coated substrate plate comprises: (1) a holey microplate made of either an organic polymeric or inorganic material and having a set of wells arranged in rows and columns, (2) an understructure support plate made of a glass material, with a number of porous patches, arranged at locations corresponding to each well of the holey microplate.

The invention also pertains to a method of making the substrate used in the device. The method comprises the following steps: providing a template for forming a number of porous patches; providing a flat, rigid, non-porous understructure; applying within said template a layer of material with granular particles to a top surface of the inorganic understructure. The template serves as an adaptor that defines the location of each porous patch so as to correspond or conform with the arrangement of wells in a microplate. The template can be made from a metal, non-metal, or other materials (e.g., solid glass). After the porous material is applied to the understructure, the granular particles, depending on the nature of the material, may be consolidated to form a porous disc or wafer attached to the understructure. The understructure with porous patches, afterwards, can be assembled or attached with a holey microplate to form the present device. Attachment of the holey microplate can be accomplished by means of state-of-the-art adhesive, sonic welding, infrared welding, or thermal bonding techniques.

According to a preferred embodiment, the method to make the porous-coated bottom plate comprises: (1) providing frits of a predetermined size in a frit suspension; (2) depositing the suspension onto the understructure (e.g., a planar glass support) at defined locations to form a number of patches of frit particles; (3) consolidating or sintering the frit particles together to form a porous wafer, and simultaneously bonding said porous wafer to said understructure. The sintering step to consolidate the porous layer is preferably performed at a relatively high-temperature (e.g., ~645° C. to ~750° C.).

Alternatively, the method comprises: (1) providing an adapter having a number of wells; (2) locating the adaptor on a support substrate; (3) applying a layer of material particles with a predetermined size within each well of the adaptor, the particles being in the form of either a dry powder or solvent suspension; (4) sintering the whole system at a temperature sufficient to adhere the particles into a porous wafer, and to attach said porous said glass support plate; and (5) removing said adaptor either before or after sintering. The individual material particles are joined together while preserving voids and void channels, for a certain amount of porosity between the individual particles. Preferably, pressure is applied to the adapter to physically press against the support plate. The thickness or height of each porous patch in each well should be uniform. This can be accomplished by means of a height regulator device. The thickness of the porous layer is preferably defined by the thickness of the adaptor itself. The adaptor can be made of a metal, a glass with a high melting temperature (e.g., ≧800° C. (Corning Code 1737)), or a ceramic material.

In another embodiment, the method can be adapted to manufacture a support plate having an organic or polymeric-porous layer. The method would comprise: (1) providing an organic or polymeric layer formed from individual granular particles that are adhered together to form a porous matrix; (2) placing the porous layer on a understructure support plate; (3) attaching the porous layer to the support plate by means of applying pressure and either (a) a thermal bond using a heated platen or adaptor with the configuration of a microplate, or (b) adhesive chemistry using a "stamp" adaptor with the same configurations of a microplate. In either approach, (a) or (b), a section of the porous layer will be separated from other areas. That is, the sections of the porous layer that form the bottom surface of each well in a microplate remain porous, while communication between the porous layers among the wells is severed. The sections of the porous layer that contact a holey microplate are sealed to prevent cross-talk. According to the thermal bonding approach, the heated platen will melt and seal the areas of the porous layer that it contacts. According to the stamping approach, the adaptor transfers an adhesive composition or solution to areas of the polymeric porous layer to which a holey microplate frame will attach. The adhesive composition fills, occupies and seals the voids or pores of the substrate at those areas, preventing cross-communication between wells. Hence, the porous layer is sandwiched between the microplate frame and the understructure support plate.

Additional features and advantages of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Section I

Introduction

Figure 1:
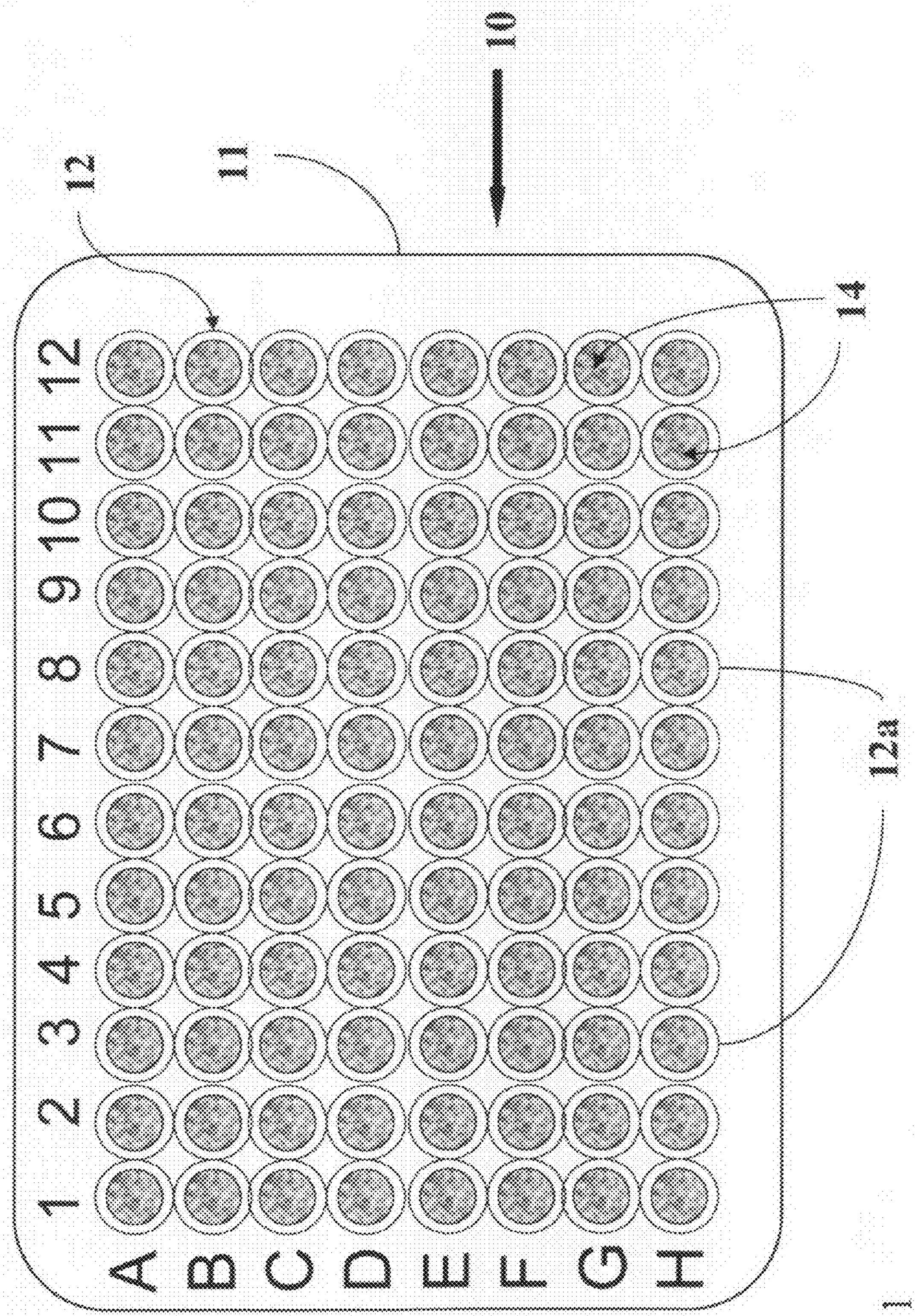
FIG. 1 shows an overview of an embodiment of a plate 10, according to the invention, having 96 wells (8×12).

A substrate plate device, as well as methods for its manufacture and use, is provided. In the following description, we will first discuss the device generally and in particular by examples, followed with a description of methods for its manufacture. Next, we describe some illustrative applications, with empirical examples, in which the present device may be employed.

Before describing the present invention in detail, it is understood that the terminology used herein is for the purpose of describing particular embodiments only, and is not intended to be limiting. As used in this specification and the appended claims, the singular forms "a," "an," and "the" include plural referents unless the context clearly indicates otherwise. Unless defined otherwise in context, all technical and scientific terms used herein have their usual meaning, conventionally understood by persons skilled in the art to which this invention pertains.

The term "microspot" refers to a discrete or defined area, locus, or spot on the surface of a substrate, containing biological or chemical probe species.

The term "probe" generally refers to a biological or chemical molecule or entity (e.g., O-protein coupled receptors (GPCR), biological membranes, lipids or lipid membranes, cell lycate, oligosaccharides, antibodies, proteins, or nucleic acids), which according to the nomenclature recommended by B. Phimister (*Nature Genetics* 1999, 21 Supplement, pp. 1-60.), is immobilized to a substrate surface. Preferably, probes are arranged in a spatially addressable fashion to form an array of microspots.

The term "target" generally refers to a biological or chemical species (e.g., antibodies, proteins, toxins, pharmaceutical compounds) in a sample of interest.

The terms "porous layer," "porous patch," "porous substrate," "porous surface," or "porous wafer," as used herein refers to a porous solid or semi-solid material (e.g., micro- or nano-scale pores), which is part of a planar substrate or plate, and can form a stable substrate for immobilizing probes.

Section II

Description

One of the primary uses of the present inventive device is for conducting high-throughput, surface-mediated biological assays, in particular, assays in microarray-format. For this purpose, biological or chemical probes are immobilized at certain predetermined or defined loci on a porous substrate or surface in each well of the microplate. The porous substrate surface, according to some embodiments, can have a modified surface chemistry to enhance the immobilization probes. The probe molecules are designed to react or bind with a target or analyte molecule, which is present in a sample. Generally in biological assays, target molecules or reference molecules, which co-exist with the targets in the sample, are labeled with an optically active marker, such as a fluorescent dye. The fluorescence or luminescence of the marker, for example, is increased during the reaction between the probe and the target (or reference molecules). A qualitative and/or quantitative analysis of the composition of the sample fluid can thus be carried out by illuminating and optically imaging or scanning the contents of each well.

According to the present invention, the substrate plate device comprises: (1) a frame or plate having a number of holes, the frame has an array of wells arranged in rows and columns; (2) an understructure support, upon which is applied granular particles (e.g., frit) that are adhered together to form a number of porous patches on the support surface at defined location(s), each corresponding to a bottom of a well in the frame of the holey microplate. The frame and understructure support each or both can be made from a glass, ceramic, crystalline, or polymer plastic material, or combination of these materials. The substrate plate device according to the present invention finds particular use in surface-mediated bioassays including microarray-based bioassays for basic research, pharmaceutical, clinic and diagnostic applications. Additionally, the device of the present invention offer significant advantages for surface-mediated bioassays. Compared to traditional glass or polymer bottom microplate, the use of porous substrate generally gives rise to much higher loading capacity, as well as higher binding specificity and accessibility of target molecules to the probes immobilized on surfaces of the porous substrate. In addition, the use of glass bottom support plate not only offers excellent optical properties of glass materials which are desirable for conventional and popular optical-based detection, but also provides excellent overall flatness cross the whole microplate, that is reducing the variability from well to well.

The present invention also describes, in particular, biological membrane or membrane-protein microarrays deposited on bare, chemically-unmodified porous substrates. Current state-of-the-art belief is that surface modification of porous substrates is preferred for biological microarrays. The present invention demonstrates that biological membrane microarrays can be fabricated on unmodified porous substrates without the loss of either assay sensitivity or binding specificity. The use of an unmodified porous substrate surface has several associated advantages. The following are just a few examples which are not to be limiting. First, an unmodified substrate can have a potentially unlimited shelf-life, since no surface chemistry or other modifications are present which may degrade, become oxidized or contaminated over time. Although a bare porous surface could also be contaminated, the substrate can be treated with a simple wash or cleaning step before use. In contrast, modified or coated substrates generally have a limited shelf-life due to contamination or reaction with the environment, which are difficult, if not impossible to restore.

The present invention also describes the fabrication of O-protein coupled receptor (GPCR) microarrays on bare porous layer, and the use of GPCR microarrays for both ligand agonism and compound screening. Biological membrane microarrays on bare or untreated porous substrate have not been demonstrated to date. The bare porous layer physically traps biological membranes, especially GPCRs, inside the porous matrices, instead of merely being immobilized on the top surface of the porous layer. Once within the matrices, biological membranes, however, still have a naturalistic degree of movement, hence the GPCRs retain full bio-functionality and both sides of the biological membrane fragment are fully accessible to a target compound or biological species.

A. —Porous Substrate-Presenting Microplate

In general terms, the present assay plate device comprises: a frame having a number of wells, each defined by at least a sidewall; a planar substrate having a surface with a number of first and second areas. The first areas each have a porous layer or patch for immobilizing probe species and the second areas being without such a porous layer. The first and second areas are adjacent to each other, and the second areas, as part of an understructure, serves as a support for each of said porous layers. The porous layer in each first area forms at least a partial over-layer of the second area. The frame and planar substrate are joined together forming a multi-well plate, in which each first area forms part of a bottom surface of said wells.

Figure 2:
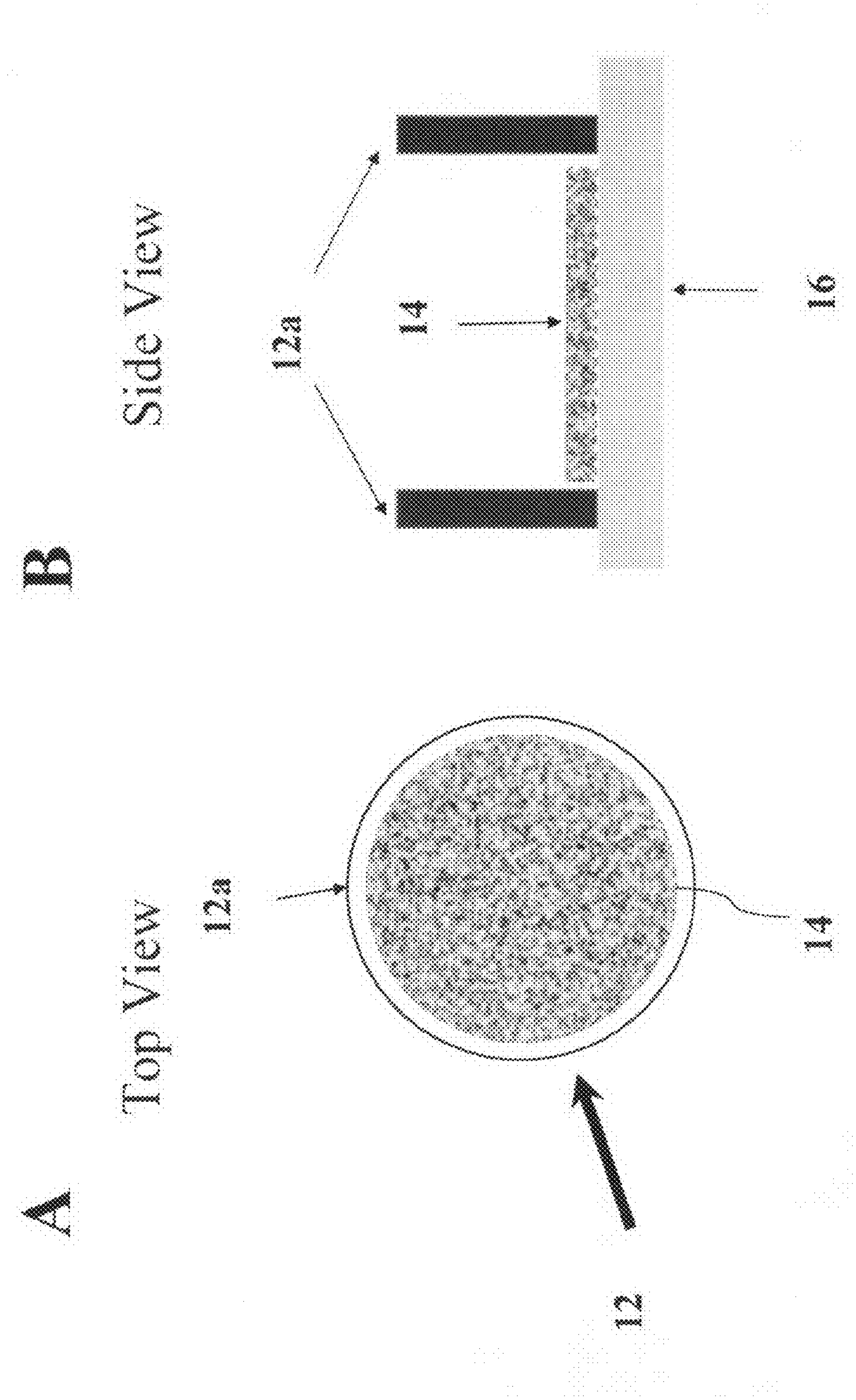
FIG. 2A shows a view looking into a well 12 of the plate of FIG. 1, within which a three-dimensional, porous layer 14 has been prepared and situated, covering substantially the entire surface area of the bottom 16 of the well.
FIG. 2B shows a side cross-sectional view of the well of FIG. 2A, wherein the porous layer forms part of the bottom support surface.

FIG. 1 is an illustration of an assay plate device according to an embodiment of the present invention. The illustration shows plate 10 with alpha-numerical labeling on a top surface, and having 96 wells (8×12), but the device may be configured with columns and rows of wells according to any microplate format. Preferably, the arrangement conforms to an industry-standard format (e.g., 384, 1536). FIG. 2A is an enlarged view of one of the wells 12, defined by a sidewall 12*a* in the microplate 10. The well has a porous layer or wafer 14 forming part of the understructure or bottom 16 of the well 12. This concept is more clearly illustrated in a schematic representation of FIG. 2B, which is a side cross-sectional view of the well 12.

In accordance with various embodiments, the entire device, including holey plate frame 11, understructure, or porous layer, may be constructed from a variety of polymer or inorganic materials or a combination of both. That is, for example, the understructure and porous layer may be inorganic, while the holey plate can be plastic. Having interconnected channels, the porous layer should preferably be formed of a kind of solid material with a granular morphology. (See e.g., U.S. Patent Publication No. 2003-0003474 A1.)

In some embodiments the solid material may be either a polymeric material, while in other embodiments, it may be a frit-based material. Preferred organic constituents may be selected from, for example, hydrophilic polyethylene, polystyrenes, polypropylenes, acrylates, metharcylates, polycarbonates, polysulfones, polyester-ketones, poly- or cyclic olefins, polychlorotrifluoroethylene, polyethylene terephthlate, or polymer compositions such as described in U.S. Pat. No. 6,653,425, No. 6,166,125, No. 6,593,415, or No. 6,590,036, incorporated herein by reference.

As for inorganic materials, a variety of glass types, such as a silicate, aluminosilicate, borosilicate, or boro-aluminosilicate, is preferred, although glass-ceramic, ceramic, semiconductor or crystalline materials such as silicon also may be employed. The particular glass type may be selected to impart desired material characteristics, such as coefficients of thermal expansion (CTE), durability, or chemical reactivity (e.g., leaching or background signal/noise), which are adapted to or satisfy specific parameters for manufacture or certain assay protocols or conditions.

Glass, glass-ceramics, or high-purity fused silica, which have properties for light transmission or optical waveguiding, or organic materials, such as optically clear polymers or plastics of uniform index having functional groups that do not generate a high background auto-fluorescence at interrogation wavelengths or scatter centers from crystallite phase separations are preferred.

In manufacture, one may use thermally extrudible or moldable optical plastics that avoid incorporation of brighteners or whitening reagents. Alternatively, after fabrication, the various material surfaces and may be treated with a reducing agent, such as a borohydride (e.g., $NaBH_4$), to remove background signals.

The porous layer is either a) unmodified or b) modified with a surface chemistry that enhances the attachment of biological species to the porous layer. The surface chemistry may be selected from a silane, a polymer, or a biological coating. The silane coating may be selected from the group consisting of: 3-acyloxypropyl-trimethoxysilane, allyltrichlorosilane, 3-aminpropyltriethoxysilane, N-(6-aminohexyl)aminopropyl-trimethoxysilane, bis(triethoxysilye) methane, 2-(3-cyclohexenyl)ethyl)triethoxysilane, 3-glycidoxypropyl-trimethoxysilane. The polymer coating may be selected from the group consisting of: chitosan, epoxy-presenting polymers, an anhydride-presenting polymer, NHS-ester-presenting polymer, aldehyde-presenting polymer, poly-ethylene-amine, or poly-lysine. The biological coating may be selected from the group consisting of: antibodies, protein-A, protein-G, lectin, wheat-germ-agglutinin. The frame is joined to the substrate support at least a number of the second areas by means of at least one of the following techniques: thermal-welding, sonic-welding, infrared-welding, or chemical adhesive, leaving the first area porous layers exposed.

B. —Methods to Make Porous Substrate-Presenting Glass Bottom Plate

The present invention also provides a method to manufacture a bottom support plate having at least one porous patch located at the defined locations corresponding to a bottom of a well of a microplate. According to one embodiment, the method comprises: providing frit particles of a predetermined size (e.g., preferably in the range of about 0.5 to about 3.5 or 5.0 microns) suspended in an organic solvent; depositing the suspension on an understructure support (e.g., preferably a glass pane or slide), at defined locations to form a number of flit-patches; binding individual frit particles into a porous matrix and attaching the porous matrix to the understructure support.

The frit could be any glass composition, but preferably are chosen from borosilicate, aluminosilicate, boroaluminosilicate, or silicate flits or pure silica powder. The solvent used to suspend the solid beads may be, for example, either texanol/enphos PVB or isopropanol. The frit particles may be deposited in patterns using an application process, such as a screen printing technique, using a screen containing domains with a certain mesh size, or a tape casting device. The granular flit particles are bound to each other during a heat-induced fusion process, such as sintering. One may manipulate the temperature of the sintering process so as to control the degree to which individual particles fuse together, hence influence the amount of consolidation and porosity. The sintering step is usually conducted at about 600-800° C., preferably 675-740° C., depending on material composition. At lower temperatures, one can achieve a high porosity of up to 98% or 99% voids throughout the resultant substrates.

Alternatively, the method to make the porous-coated bottom plate comprises: (1) providing an adapter made of metal and having a number of wells; (2) placing the adaptor on a support substrate; (3) filling each well of said adaptor with granular particles either as a powder or as a suspension insolvent; (4) heat treating the whole assembly at a high temperature to fuse the particles together, and the resultant porous layer with the support plate; and (5) removing the adaptor. Preferably, the adapter is physically pressed against the support substrate. A leveler device can be used to ensure that the granular particles in each well are of a consistent or uniform thickness. To fabricate a porous polymeric-coating layer, the method can be adapted. First, provide a porous sheet of polymeric material, place the porous sheet onto an inorganic understructure support, attach the porous sheet to the understructure support by means of either using (a) a heated platen having a configuration as that of a holey microplate, which melts and seals the voids in the areas of the porous sheet that come into contact with the platen, or (b) a "stamp" adaptor with the same configuration as of a holey microplate to transfer an adhesive to defined area of the porous sheet, which likewise seals the voids, isolating porous areas from each other.

C. —GPCR Microarray on Modified Porous Substrate Surface

Fabrication of biological arrays, especially membrane-protein or GPCR microarrays, can be particularly challenging. This is mainly due to the fact that the GPCR needs to be associated with a lipid membrane to retain its correct folded conformation and function. Previously, workers in this area have attempted covalent immobilization of the entire membrane to a substrate surface. Such a technique is not desirable because lateral mobility is an intrinsic and physiologically important property of biological membranes. In addition, the GPCR-G protein complex should be preserved after being arrayed onto a surface because the correct configuration of the receptor and G protein is a prerequisite for the binding of agonists to the receptor with physiological binding affinity. The surface could have a significant impact not only on the structure and functionality of the receptors, but it also plays a critical role in the structure and mechanical stability of the immobilized lipid membranes.

In U.S. Patent Publication Nos. 2002-0019015 A1, and 2002-0094544 A1, Fang et al. described the fabrication of biological membrane-protein microarrays on two-dimensional, amine-coated, inorganic substrates (e.g., gama-aminopropylsilane (GAPS) surfaces), using robotic printing techniques. They demonstrated that a GPCR microarray can be made using cell-membrane fragments or preparations, while maintaining desired structures, lateral fluidity, and significant mechanical stability. The microarrays allow specific binding of ligands to their cognate receptors in the array. The binding affinities and profiles of these ligands are similar to those obtained using traditional methods, including solution-based or cell-based assays.

Using a fabrication technique, like screen printing or tape casting, such as mentioned in U.S. Patent Publication No. 2003-0003474 A1, incorporated herein by reference, one can prepare an array of 96, 384, or 1536, patches of silica friton an inorganic support plate. Silica fit, according to an example, is suspended and homogenized in an organic-based solution to spread the flit particles in a mask or screen. After printing, the frit patches are sintered, for example at a temperature of about 650-750° C., to harden, fuse together, or consolidate the particles to a desired density to form a porous wafer or matrix stably associated with the support plate. Each porous wafer is coated with GAPS. Afterwards, the porous-wafer-presenting support plate is subsequently assembled with a well plate, such that each porous wafer forms part of the bottom of each well.

A biological membrane array is deposited onto each porous wafer. The array content can be the same or different from well to well. The biological membrane could be a cell-membrane fragment preparation, a lipid vesicle containing reconstituted membrane-protein, or a lipid micelle containing a membrane-protein, an exosome vesicle particle containing at least a membrane-protein of interest. For binding assays using a GPCR microarray, a cocktail solution of labeled ligands in either the presence or absence of a target compound is applied to each array. After incubation the solution is aspirated from each well and each array is washed three times with an aqueous washing solution and dried. Afterwards, each array is examined or imaged using a CCD-camera-based detection system or PMT-based scanner.

Figure 3:
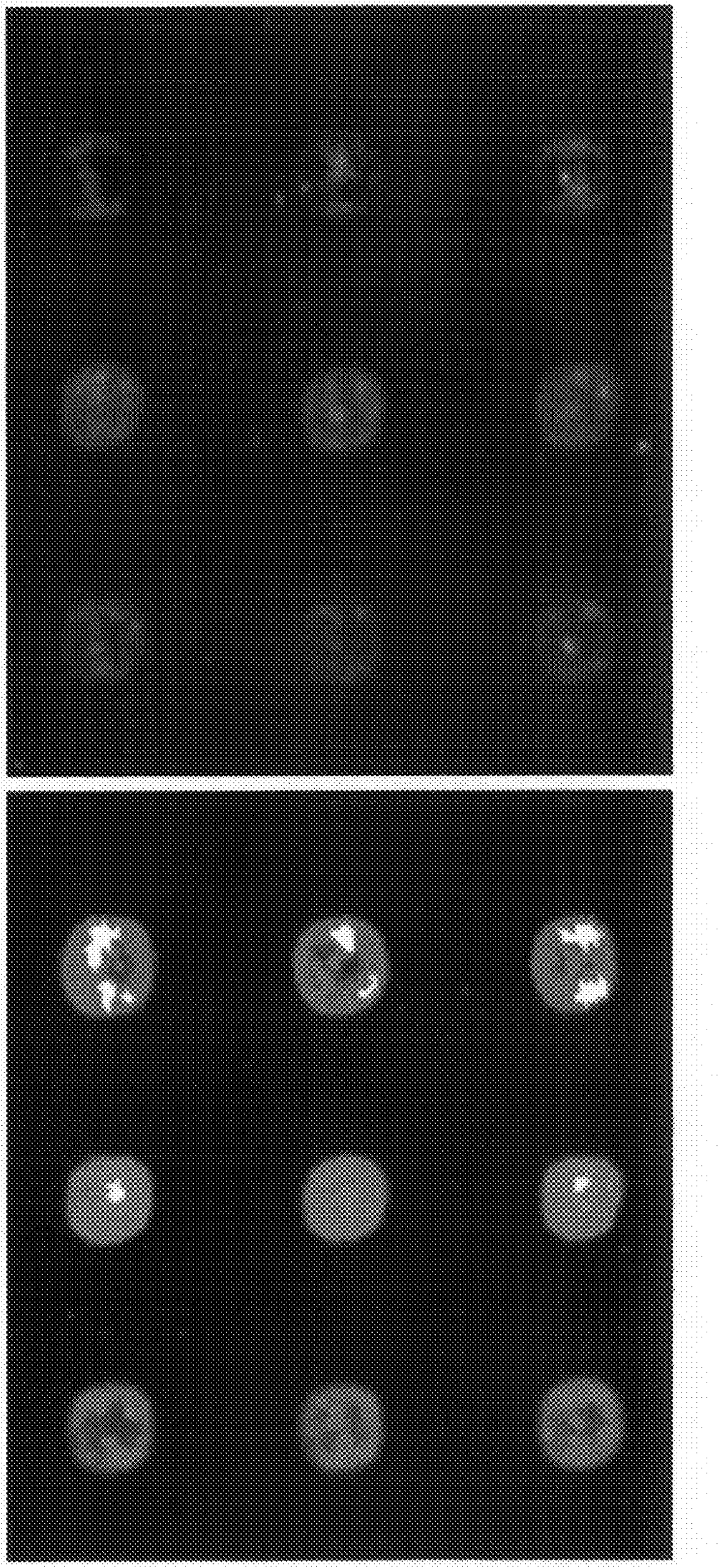
FIGS. 3A and B, respectively, are false-colored fluorescence images of a microarray of GPCRs after being assayed with a "cocktail solution" of labeled ligand in the absence and presence of unlabeled ligands. The cocktail solution of labeled ligand contains 2 nM Cy3B-telenzpine, and 4 nM Cy5-naltrexone. The unlabeled ligands include 1 μM telenzpine and 1 μM naltrexone. Each GPCR microarray in each well includes muscrinic receptor subtype 2 (M2), delta 2 opioid receptor (OP1) and muscrinic receptor subtype 1 (M1) from left to right in column. Each receptor has four replicates. Telenzpine is an antagonist of M1 and M2, whereas naltrexone is an antagonist of OP1.
Figure 4:
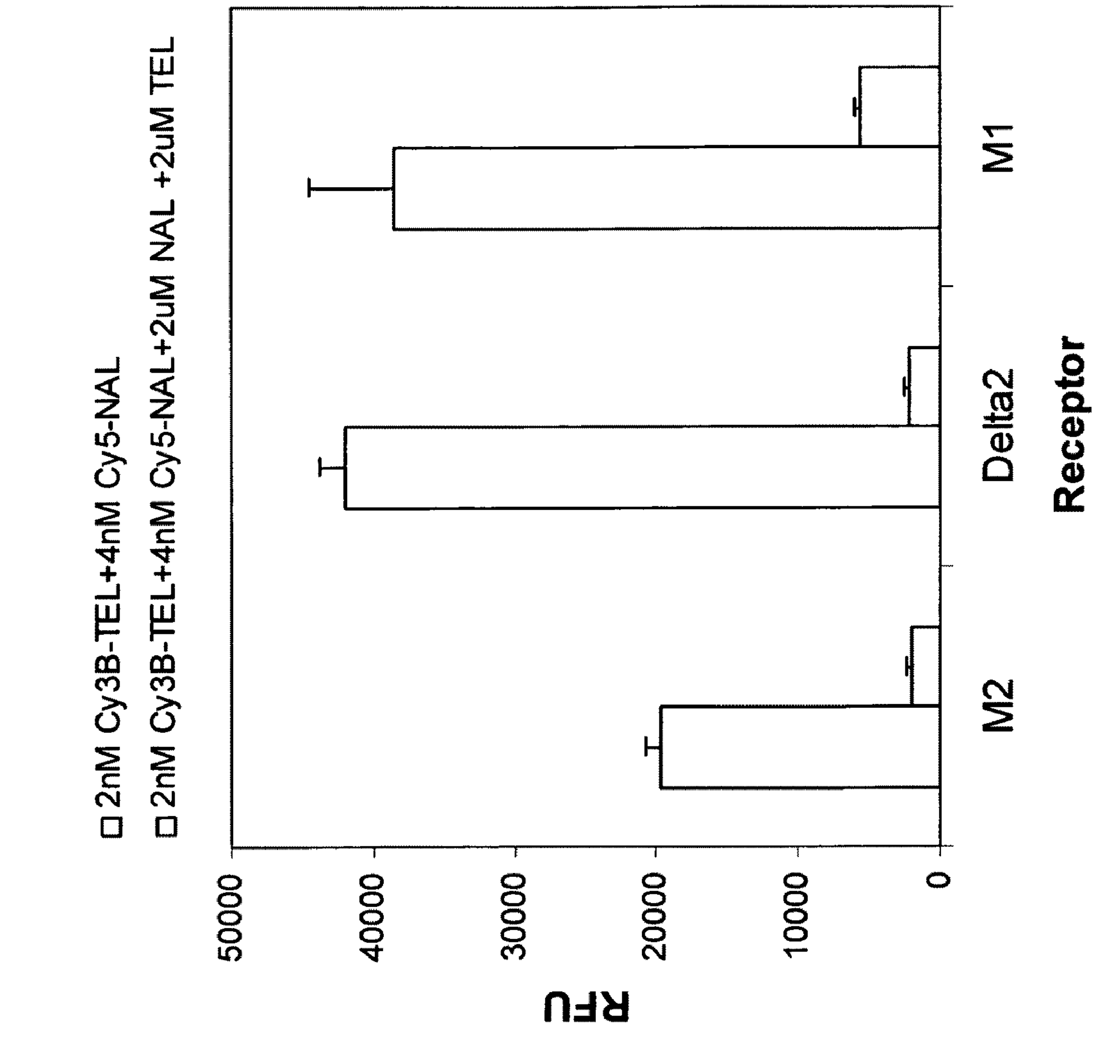
FIG. 4 summarizes in a graph the assay results generated from FIGS. 3A and 3B. The graph presents the signal intensity of three receptors as a function of microspots after the microarrays are assayed with the cocktail solution of labeled ligands in the presence (dark bar) and absence (light bar) of unlabeled ligands.

In the examples shown in FIGS. 3 and 4, a microarray of three types of GPCRs is printed in each well using a quill-pin printer (Cartesian Technologies Model PS 5000) equipped with software for programmable aspiration and dispensing. The three receptors are muscrinic receptor subtype 2 (M2), delta 2 opioid receptor (OP1) and muscrinic receptor subtype 1 (M1). Each receptor has four replicates. FIGS. 3A and B, respectively, show false-colored fluorescence images of a microarray of GPCRs after being assayed with a "cocktail solution" of labeled ligand in both the absence and presence of unlabeled ligand. The cocktail solution of labeled ligand contains 2 nM CyB-telenzpine, and 4 nM Cy5-naltrexone. The unlabeled ligands include 1 μM telenzpine and 1 μM naltrexone. FIG. 4 summarizes the assay results generated from FIGS. 3A and 3B. FIG. 4 presents the signal intensity as a function of microspot after the microarray was assayed with the cocktail solution of labeled ligand in the presence (dark bar) and absence (light bar) of unlabeled ligands. As demonstrated by the total binding capacity of labeled ligands to their cognate receptors, the loading capacity of GPCR in each microspot is significantly higher ($\geqq$50 times) than that on a two-dimensional GAPS-coated surface. The binding specificity of labeled ligands to their corresponding receptors is virtually the same as that measured in solution, such as fluorescent polarization or radio-active assays. The assay signal-to-noise ratio is significantly better than that achieved on two-dimensional surface.

D—GPCR Microarray on Unmodified, Bare Porous Substrate Surface

In contrast to a coated porous surface, such as described in the preceding section, another aspect of the present invention uses unmodified or bare porous surfaces for membrane-protein arrays. To achieve maximum binding capacity and desired stability of proteins on a surface while largely preserving structure and functional activity, conventionally, a biological microarray requires a solid support surface that is carefully modified or engineered with a surface chemistry. The interaction of proteins with a surface, however, complicates the preparation of protein microarrays. This is because (i) proteins could denature at the interface between an aqueous solution and a solid surface, and (ii) random immobilization of proteins on a surface may cause the active site(s) of the proteins to be inaccessible for binding. By using a bare porous substrate, one may be able to physically trap the biological membranes in the porous matrix, hence the biological membranes can largely avoid steric interference from the surface when reacting with target species while maintaining bio-functionality and an predetermined array macro-configurations.

Figure 5:
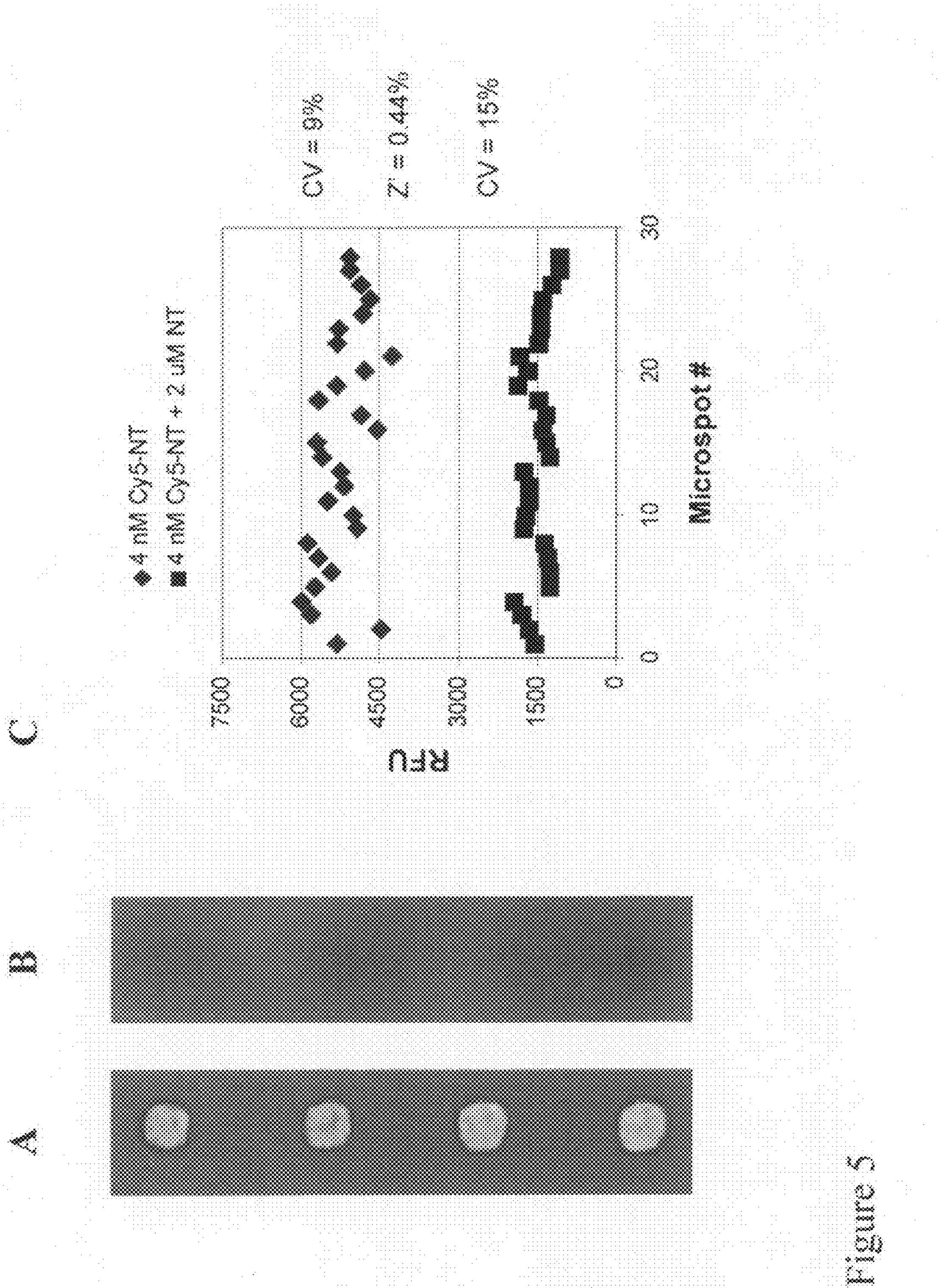
FIG. 5A is a false-color fluorescence image of an NTR1 microarray on a bate silica-based porous substrate after being assayed with 4 nM Cy5-NT2-13. The corresponding binding signals are termed as total binding signals.
FIG. 5B is a false-color fluorescence image of a second NTR1 microarray after being assayed with 4 nM Cy5-NT2-13 in the presence of 2 μM unlabeled NT. The corresponding binding signals are termed as non-specific binding signals.
FIG. 5C is a graph summarizing the results of FIGS. 5A and 5B. The total and non-specific binding signals are presented as a function of microspot number. Two subsets of seven individual microarrays, each with 4 replicates, were analyzed and plotted.

Using a microplate similar to that described in section C, above, except without a coating on the porous wafers, one can directly deposit a biological membrane microarray on the bare, unmodified porous wafer in each well. The porous substrates are not modified with any chemical or biological material to enhance the immobilization of biological membranes. Before array printing, the plate surface is treated with UV/Ozone exposure for about five minutes to decontaminate the surface. In the examples shown in FIG. 5, a microarray of neurotensin receptor Subtype 1 (NTR1) in three or four replicates is printed in each well, and assayed with a solution containing 4 nM Cy5-labeled neurotensin (Cy5-NT) in the presence or absence of unlabeled excess neurotensin (2 μM). As shown in the images of FIGS. 5A and 5B, the binding of Cy5-NT to NTR1 in the array can be inhibited by the unlabeled excess neurotensin, which suggests that the binding is specific. As shown in the graph of FIG. 5C, the assay variance (CV) is about 9% for total binding of Cy5-NT to the NTR1, whereas the CV is about 15% for the nonspecific binding of Cy5-NT to NTR1. The assay robustness (Z' factor) is about 0.44, which is comparable with the industrial standard for any given GPCR-based assays, which is about 0.4. (See, Zhang, J. et al. (1999) *J. Biomol Screening* 4, 67-73.)

Figure 6:
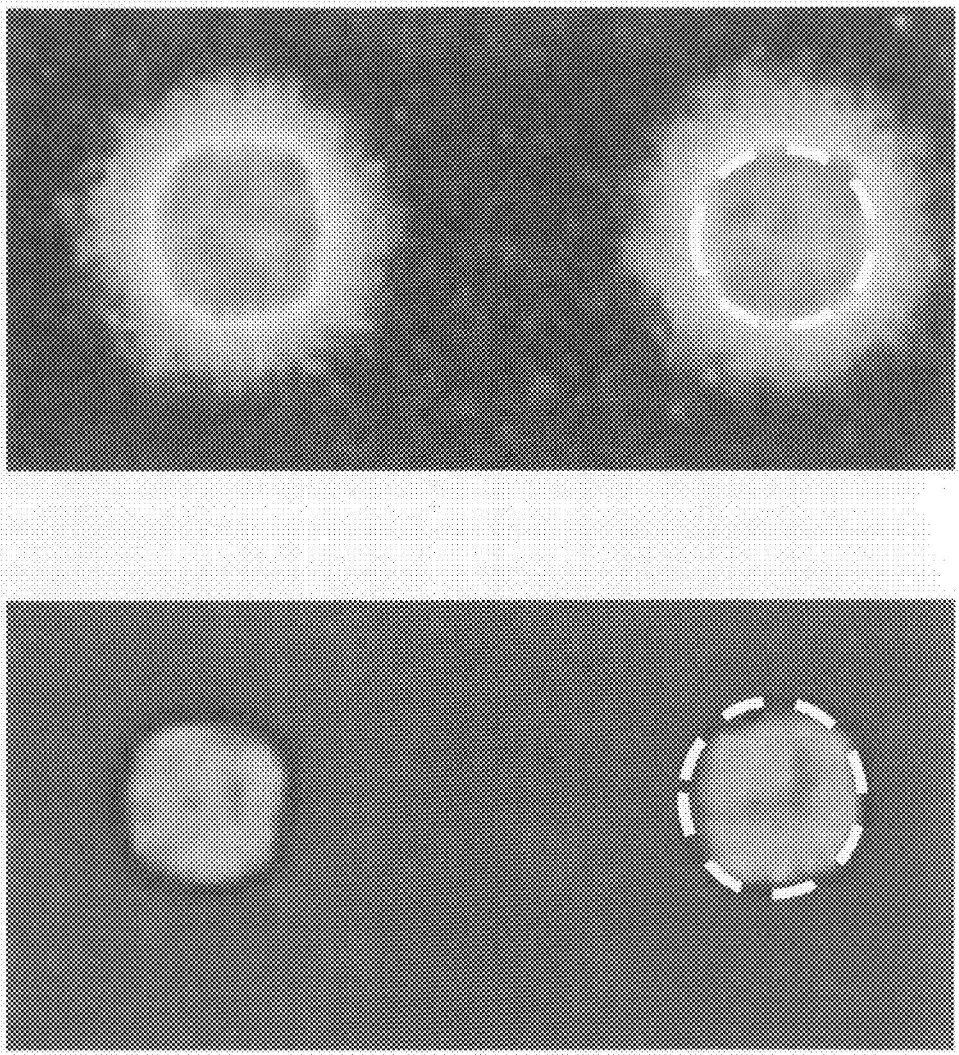
FIG. 6A is a false-color fluorescence image of an NTR1 microarray on a bare silica-based porous substrate after being assayed with 4 nM Cy5-NT2-13. The NTR1 membrane preparation was reformulated with a $G_{\alpha i}$ protein.
FIG. 6B is a false-color fluorescence image of the same NTR1 microarray as in FIG. 6A, after sequential being assayed with 1 nM mouse anti-$G_{\alpha i}$, followed by 1M Cy5-anti mouse IgG. The binding of Cy5-anti-mouse IgG to mouse anti-Gi antibody pre-bound to the microspots gave rise to much larger staining area than the binding of Cy5-NT 2-13 to the receptors in the microspot.

The potential mechanism of GPCR microarrays on bare porous substrates is further examined. First, a microarray of NTR1, fabricated using NTR1 membrane preparations reformulated with a mouse anti-Gi antibody, is assayed using a solution of about 4 nM Cy5-NT in a binding buffer. Then, the same array is sequentially incubated with a solution containing 1 nM Cy5-anti-mouse IgG. The staining area of Cy5-anti-mouse IgG is found to be larger (~50% more) than that of Cy5-NT binding to NTR1 receptors in the same microspot, suggesting that the antibody can diffuse beyond the printing area, however, the GPCR membrane fragment stays in the predetermined microspot perimeter (a.k.a., pin contact area) as shown in FIG. 6.

Figure 7:
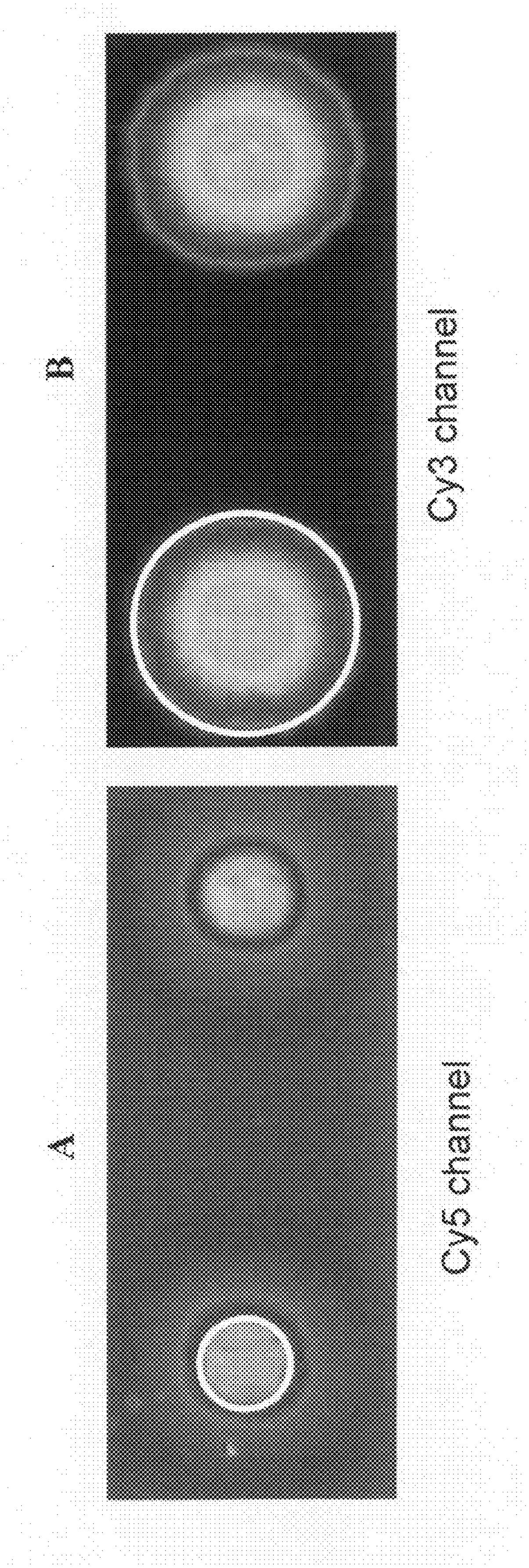
FIGS. 7A and 7B are false-color fluorescence images in both Cy3 and Cy5 channels of a delta2 opioid (OP1) microarray on a bare silica-based porous substrate after incubation with 4 nM Cy5-naltrexone. The OP1 membrane preparations are reformulated in a solution containing 0.1% Cy3-labeled BSA. Cy5-naltrexone is fluorescent analog of naltrexone, an antagonist of the OP1 receptor. The results show that the distribution of Cy3 BSA in the microspot area (FIG. 7B) has a much larger staining area than the binding of Cy5-nalrexone to OP1 in the same microspot (FIG. 7A).

Second, a microarray of delta-2-opioid receptor (OP1), fabricated using OP1 membrane preparations reformulated with Cy3-labeled bovine serum albumin (Cy3-BSA), is assayed with a solution containing about 4 nM Cy5-naltrexone. The staining area of Cy3-BSA is found to be much larger (~100% or more) than that of Cy5-naltrexone binding to the OP1 receptors in the same microspot, suggesting that the BSA can diffuse beyond the printing area, however, the GPCR membrane fragment stays in the predetermined microspot perimeter as shown in FIG. 7. In summary, these results suggest that the diffusion of probe molecules during printing is size-dependent. These results indicate that individual proteins such as BSA and antibodies can diffuse inside the porous layer beyond the printing area, but not membrane fragments. It is known that the size of GPCR membrane fragments are generally in the range of 50-100 nm, which is much larger than BSA (~5 nm) and antibody (~10 nm).

Figure 8:
FIG. 8 is a scanning electron microscopic (SEM) image of the cross-section of a silica-based porous substrate (located 25 μm below the top surface of the substrate) after incubation with a 40 nm gold nanoparticle. From the image, one observes 4 nanoparticles, suggesting that the gold nanoparticles can diffuse from the top surface and become physically trapped inside the porous matrix.

The next phenomenon we examined is how particles with larger size can stay within the voids of a porous matrix during printing. For this purpose, gold nanoparticles with a diameter of 40 nm are used as a model to stand for GPCR membrane fragments, since these particles are either similar to or slightly smaller in size than a GPCR membrane fragment, and can be distinguished by scanning electron-microscope (SEM). As shown in FIG. 8, we observed that gold nanoparticles can diffuse to about 25 μm deep into the porous matrix from the accessible, exposed surface and become physically ensnared inside the porous matrix. This result suggests that biological membranes including GPCR preparations can diffuse and become physically trapped inside the porous matrix after being printed on the surface. This signifies that the probes would not need complicated attachment chemistry. The immobilization of a certain percentage of biological membrane probes on the unmodified surface may also contribute to the physical stability of the microarrays.

E. —Examples of Other Bio-Assays

Alternate applications that may benefit from the present invention may include other types of biological binding-assays useful for either genomic or proteomic research. Examples of some of this and other arrays and applications follow.

As mentioned before, for conducting automated high-throughput surface-mediated bioassays, biological or chemical probe molecules are immobilized onto the porous substrate at the determined loci or areas. A sample solution containing target molecule(s) is applied to each well of the substrate plate device. A target or analyte present in the sample reacts with the probe molecules. In general, the target molecules or a reference molecule co-existed with the targets in the sample are tagged with an optically active compound, of which the fluorescence or luminescence is increased during the reaction between target (or the reference molecules) and probe, for example. A qualitative and/or quantitative analysis of the composition of the sample fluid can thus be carried out by illuminating and optically scanning the contents of the wells.

In an embodiment, the target analyte being detected is a nucleic acid, when a DNA probe microarray is used in which a set of probe nucleic acid molecules with known sequences are tethered or immobilized onto a surface in confined locations. The target sequence may be a portion of a gene, a regulatory sequence, genomic DNA, cDNA, RNA including mRNA and rRNA, or others. The target sequence is preferred used to be in a single-stranded format; however, the target sequence in a double stranded conformation (e.g., genomic DNA) may be used after denaturation. The target sequence is preferably labeled with a detectable moiety or moieties, such as fluorescence dye molecule(s) to allow detection of the binding of the target sequence to the probe microspots directly using fluorescence imaging techniques, or with biotin moiety(ies) in which a sequential detection step using labeled anti-biotin or anti-biotin coated gold nanoparticle is required for detection the binding of the target sequence to the probe microspots (Bao et al. Anal. Chem. 2002, 74, 1792-1797). By "probe nucleic acid" or "probe sequence" herein means a nucleic acid sequence with known sequence or defined sequence. Preferably, the probe nucleic acid is a cDNA, a oligonucleotide with defined sequence, or a modified oligonucleotide with defined sequence. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron 1993, 49, 1925), peptide nucleic acid backbones and linkages (Egholm, J, Am. Chem. Soc. 1992, 114, 1895); Nielsen, Nature, 1993, 365, 566). As will be appreciated by those in the art, all of these nucleic acid analogs may find use in the present invention.

In another embodiment, the target analyte is a pharmacological compound or ligand, when a probe protein microarray is used. By "target compound" or "target ligand" herein means a chemical or biochemical or biological compound whose identity/abundance/binding affinity and specificity is to be detected. The target compound can be synthetic, naturally occurring, or produced biologically. The target compound may be a abuse drug, a drug candidate, a chemical (an organic or inorganic compound including ionic salt), a biochemical (e.g. synthetic lipids, oligosaccharides, peptides, amino acids, nucleotides, nucleosides, etc), or a biological (e.g., a naturally occurring lipids, a protein, an antigen, an antibody, a growth factor, etc.). The target compound may be an activator, an inhibitor, an effector, a binding partner, or an enzyme substrate of the probe protein(s). The target compound can be part of a selected or random compound library. By "probe protein" or "probe polypeptide" herein means a polypeptide with known sequence. The probe proteins may be obtained from natural sources or, optionally, be overexpressed using recombinant DNA methods. The probe proteins may be either purified using conventional approaches or un-purified (e.g. cell lysates). The probe protein includes, but not limited to, intracellular proteins, cell surface proteins, soluble proteins, toxin proteins, synthetic peptides, bioactive peptides, and protein domains. Examples of intracellular proteins include, but are not limited to: oxidoreductases, transferases, hydrolases, lyases, isomerases, ligases, kinases, phosphoproteines, and mutator transposons, DNA or RNA associated proteins (for example, homeobox, HMG, PAX, histones, DNA repair, p53, RecA, robosomal proteins, etc.), electron transport proteins (for example, flavodoxins); adaptor proteins; initiator caspases, effector caspases, inflammatory caspases, cyclins, cyclin-dependent kinases, cytokeletal proteins, G-protein regulators, small G proteins, mitochondria-associated proteins, PDZ adaptor proteins, PI-4-kinases, etc. Recombinant proteins of unknown functions may also be used. Applicable cell surface proteins include, but are not limited to: GPCRs (e.g. the aderenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc), G proteins, ion-channels (nicotinic acetylcholine receptor, sodium and potassium channels, etc), receptor tyrosine kinases (e.g. epidermal growth factor (EGF) receptor), immune receptors, integrins, and other membrane-bound proteins. Mutants or modifications of such proteins or protein functional domains or any recombinant forms of such proteins may also be used. Toxin proteins include, but are not limited to, cholera toxin, tetanus toxin, shiga toxin, heat-labile toxin, botulinum toxin A & B, delta toxin, pertussis toxin, etc. Toxin domains or subunits may also be used. In this embodiment, the probe protein microarrays may be used for identification small molecules binding proteins (Zhu, H, et al. "Global analysis of protein activities using proteome chips," Science 2001, 293, 1201-2105), or used for measuring protein kinase activities (Houseman, B. T., Huh, J. H., Kron, S. J., Mrksich, M. "Peptide chips for the quantitative evaluation of protein kinase activity," Nature Biotechnology 2002, 20, 270-274), or used for compound pharmacological profiling (binding affinity, selectivity, and specificity) and compound screening (Fang, Y., et al. "Membrane protein microarrys," J. Am. Chem. Soc. 2002, 124, 2394-2395; and Fang, Y. et al. "Membrane biochips," BioTechniques, 2002, 33, S62-865).

In a further embodiment, the target analyte is an antigen, a hormone, a cytokine, an immune antibody, a protein, a lipid, or a mixture of un-purified cell lysate, when a probe antibody microarray is used. By "target biologicals" herein means a biological from a biofluid or an organelle or a living cell whose identity/abundance is be detected. The probe antibody includes, but not limited to, an immunoglobulins (e.g., IgEs, IgGs and IgMs), a therapeutically or diagnostically relevant antibodies (e.g., antibodies to human albumin, apolipoproteins including apolipoprotein E, human chorionic gonadotropin, cortisol, a-fetoprotein, thyroxin, thyroid stimulating hormone, antithrombin; antibodies to antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates)), a antibody to any viruses (e.g. antibodies to orthomyxovi ruses such as influenza virus, paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, 6 and C), herpesviruses (e.g. Herpes simplex virus, varicella-zoster virus, cytornegalovirus, Epstein-Barr virus), rotaviruses, Norwalk viruses, hantavirus, arenavirus, rhabdovirus (e.g. rabies virus), retroviruses (including HIV, HTLV-I and -11), papovaviruses (e.g. papillomavirus), polyornaviruses, and picornaviruses, and the like), and anthrax, etc.), an antibody to bacteria (e.g., antibodies to a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. Ieprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haernophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like)), an antibody to bacteria toxin (e.g., antibodies to diphtheria toxin, anthrax toxin, tetrodotoxin, saxitoxin, bactrachotoxin, grayanotoxin, veratridine, actonitine, scorpion, sea anemone venom, scorpion charybdotxins, dendrotoxins, hanatoxins, sea anemone toxins, bololena, calcicludine, bungarotoxin, cholera toxin, conantokin, etc).

In another embodiment, the probe antibody arrays may be used for protein profiling, measurement of protein abundance in blood, measurement of cytokine abundance, detection of bacteria toxins in samples (such as environmental water, or food resources), as well as capture of leukocytes/phenotyping leukemias. These target species may be present in any number of different sample yes, including, but not limited to, bodily fluids including blood, lymph, saliva, vaginal and anal secretions, urine, feces, perspiration and tears, and solid tissues, including liver, spleen, bone marrow, lung, muscle, brain, etc. Conversely, the "probes" can also be antigens, in which the antigen arrays may be used for reverse immunoassay to measure autoimmune antibodies and allergies.

In another embodiment, a carbohydrate microarray that involve immobilization of oligosaccharides or polysaccharides on to a surface in confined locations is used for detecting the carbohydrate-binding protein target(s) in a sample (Fukui, S., Feizi, T., Galustian, C., Lawson, A. M., and Chai, W. "Oligosaccharide microarrays for high-throughput detection and specificity assignments of carbohydrate-protein interactions," Nature Biotechnology, 2002, 20, 1011-1017), and for identifying cross-reactive molecular markers of microbes and host cells (Wang, D., Liu, S., Trummer, B. J., Deng, C., and Wang, A., "Carbohydrate microarrays for recognition of cross-reactive molecular markers of microbes and host cells" Nature Biotechnology, 2002, 20, 275-281), and for identifying specific viruses or bacteria or spores.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A method of making a substrate used in a microplate, the method comprises the following steps:

providing a template for forming a number of porous patches;

providing a flat, rigid, non-porous understructure; and applying within said template a layer of material with granular particles to a top surface of the inorganic understructure.

2. The method according to claim 1, wherein said template serves as an adaptor that defines the location of each porous patch so as to correspond with an arrangement of wells in said microplate.

3. The method according to claim 1, wherein said granular particles are consolidated to form a porous wafer attached to said understructure.

4. A method for manufacturing a support plate, the method comprises:

providing an organic or polymeric layer formed from individual granular particles that are adhered together to form a porous matrix;

placing said porous layer on a understructure support plate; and attaching said porous layer to said understructure support plate by means of applying pressure and either (a) a thermal bond using a heated platen or adaptor with the configuration of a microplate, or (b) adhesive chemistry using a "stamp" adaptor with the same configurations of a microplate, where in either approach (a) or (b) a section of the porous layer will be separated from other areas.

* * * * *